United States Patent [19]

Brittain et al.

[11] 4,393,062
[45] Jul. 12, 1983

[54] PHARMACEUTICAL COMPOSITIONS AND METHOD FOR THE PRODUCTION OF AN ANTI-INFLAMMATORY EFFECT

[75] Inventors: David R. Brittain; Robin Wood, both of Macclesfield, England

[73] Assignee: Imperial Chemical Industries PLC, London, England

[21] Appl. No.: 194,211

[22] Filed: Oct. 6, 1980

Related U.S. Application Data

[62] Division of Ser. No. 964,725, Nov. 29, 1978, Pat. No. 4,251,528.

[30] Foreign Application Priority Data

Dec. 29, 1977 [GB] United Kingdom ............... 54142/77

[51] Int. Cl.³ ................. C07D 237/32; A61K 31/495
[52] U.S. Cl. .................................... 424/250; 544/237
[58] Field of Search ......................... 544/237; 424/250

[56] References Cited

U.S. PATENT DOCUMENTS

| | | | |
|---|---|---|---|
| 3,833,579 | 9/1974 | Inoue et al. | 544/237 |
| 3,864,343 | 2/1975 | Inoue et al. | 544/237 |
| 4,066,651 | 1/1978 | Brittain et al. | 426/258 |
| 4,096,143 | 6/1978 | Sato et al. | 544/237 |
| 4,182,876 | 1/1980 | Shimamoto et al. | 544/237 |
| 4,251,528 | 2/1981 | Brittain et al. | 544/237 |
| 4,293,553 | 10/1981 | Ishikawa et al. | 544/237 |

FOREIGN PATENT DOCUMENTS 1502312 3/1978 United Kingdom .

OTHER PUBLICATIONS

Jour. Khim. Farm Zh vol. 4, cl 22-26 (1970).
Chem. Abstracts vol. 73, p. 366 (77173y) 1970.

Primary Examiner—Nicholas S. Rizzo
Attorney, Agent, or Firm—Cushman, Darby & Cushman

[57] ABSTRACT

This invention relates to enzyme inhibitory, novel phthalazin-4-ylacetic acid derivatives of the general formula I:

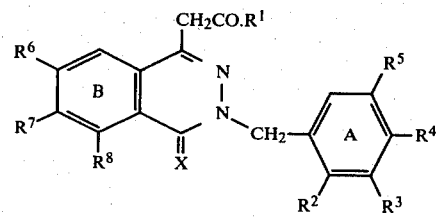

and pharmaceutically acceptable salts as appropriate, to pharmaceutical compositions thereof, and to analogy processes for their manufacture. The compounds of formula I are inhibitors of the enzyme aldose reductase in vivo and as such may be useful in the reduction or prevention of the development of the peripheral effects such as macular oedema, cataract, retinopathy or impaired neural conduction. A preferred compound is 2-(2-fluoro-4-bromobenzyl)-1,2-dihydro-1-oxophthalazin-4-ylacetic acid.

5 Claims, No Drawings

PHARMACEUTICAL COMPOSITIONS AND METHOD FOR THE PRODUCTION OF AN ANTI-INFLAMMATORY EFFECT

This is a division of application Ser. No. 964,725, filed Nov. 29, 1978, now U.S. Pat. No. 4,251,528.

This invention relates to novel phthalazin-4-ylacetic acid derivatives and, more particularly, it relates to such derivatives which possess the property of inhibiting the enzyme aldose reductase in vivo.

The enzyme aldose reductase is responsible for the catalytic conversion of aldoses, for example glucose and galactose, to the corresponding alditols, for example sorbitol and galactitol respectively. Alditols penetrate cell membranes poorly and, once formed, tend to be removed only by further metabolism. As a consequence, alditols tend to accumulate within cells where they are formed, causing a rise in internal osmotic pressure which may in turn be sufficient to destroy or impair the function of the cells themselves. In addition, raised alditol levels may result in abnormal levels of their metabolites which may themselves impair or damage cellular function. However, the enzyme aldose reductase has a relatively low substrate affinity, that is, it is only effective in the presence of relatively large concentrations of aldose. Such large concentrations of aldose are present in the clinical conditions of diabetes (excessive glucose) and galactosemia (excessive galactose). As a consequence, inhibitors of the enzyme aldose reductase are useful in the reduction or prevention of the development of those peripheral effects of diabetes or galactosemia which may be due in part to the accumulation of sorbitol or galactitol respectively. Such peripheral effects are, for example, macular oedema, cataract, retinopathy or impaired neural conduction.

It is known from our earlier work that 1-benzyl-2-oxoquinol-4-ylalkanoic acid derivatives are inhibitors of the enzyme aldose reductase (U.K. Pat. specification Ser. No. 1,502,312). We have now found that certain 2-benzyl-1-oxophthalazin-4-ylacetic acid derivatives defined hereinafter, are unexpectedly also inhibitors of the enzyme aldose reductase. This finding is particularly surprising in view of the many differences between the 2-oxoquinoline and 1-oxophthalazine ring systems. The related phthalazine derivatives, 2-benzyl- and 2-(2-pyrid-2-ylethyl)-1,2-dihydro-1-oxophthalazin-4-ylacetic acid together with their methyl and ethyl esters, are known, and their effects on the clotting system of blood have been reported (Sh. Feldeak et alia, Khim. Farm. Zh., 1970, 4, 22–26; Chemical Abstracts, 1970, 73, 77173) but, unlike the compounds of the invention defined hereinbelow, none of these known phthalazine derivatives are inhibitors of aldose reductase in vivo at oral doses of 100 mg./kg. or less.

According to the invention there is provided a phthalazin-4-ylacetic acid derivative of the formula:

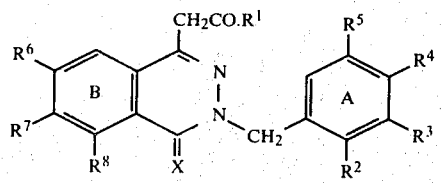

wherein $R^1$ is a hydroxy or benzyloxy radical, or a $C_{1-4}$-alkoxy radical optionally bearing an N-morpholino or di-$C_{1-4}$-alkylamino radical; the substituents $R^2$, $R^3$, $R^4$ and $R^5$ on benzene ring A are selected from any one of the following combinations:

(a), $R^2$ is a fluoro or methoxy radical, $R^3$ is hydrogen, $R^4$ is a chloro, bromo or iodo radical, and $R^5$ is hydrogen or a halogeno radical;

(b), $R^2$, $R^3$ and $R^5$ are hydrogen, and $R^4$ is a bromo or iodo radical;

(c), $R^2$ is hydrogen or a fluoro radical, $R^3$ and $R^5$ are the same or different halogeno radicals, and $R^4$ is hydrogen;

(d), $R^2$ is hydrogen or a fluoro radical, $R^3$ and $R^4$ are the same or different halogeno radicals, and $R^5$ is hydrogen; and (e), $R^2$ is hydrogen, $R^3$ and $R^5$ are independently fluoro or chloro radicals, and $R^4$ is a chloro, bromo or iodo radical; and wherein, on benzene ring B, $R^6$, $R^7$ and $R^8$ are independently selected from hydrogen, halogeno, $C_{1-4}$-alkyl and $C_{1-4}$-alkoxy radicals; or $R^6$ and $R^7$ together constitute a $C_{1-4}$-alkylenedioxy diradical; provided that at least one of $R^6$, $R^7$ and $R^8$ is hydrogen; and X is oxygen or sulphur; or a pharmaceutically acceptable base-addition salt of a compound of formula I wherein $R^1$ is a hydroxy radical; or a pharmaceutically acceptable acid-addition salt of a compound of formula I wherein $R^1$ is a $C_{1-4}$-alkoxy radical bearing an N-morpholino or di-$C_{1-4}$-alkylamino radical.

The compounds of formula I are derivatives of 1,2-dihydro-1-oxo-(or-thioxo)-phthalazin-4-ylacetic acid, which is numbered throughout this specification as follows:

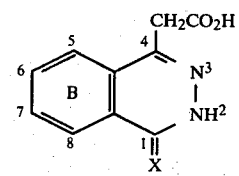

where X is oxygen or sulphur.

It will be appreciated that the compounds of formula I are capable of tautomerism to give a structure of the formula:

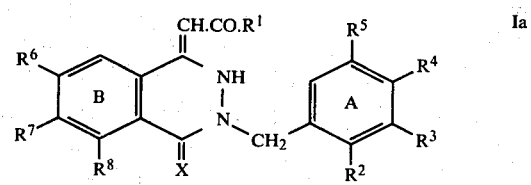

and it is to be understood that this invention embraces tautomers of formula I (endo-tautomer) or of formula Ia (exo-tautomer), or mixtures thereof.

A particular value for $R^3$ or $R^5$ when it is a halogeno radical is, for example, a fluoro, chloro, bromo or iodo radical, and especially a chloro or bromo radical.

A particular value for $R^6$, $R^7$ or $R^8$ when it is a halogeno radical is, for example, a fluoro, chloro, bromo or iodo radical; when it is a $C_{1-4}$-alkyl radical, is, for example, a methyl radical; and when it is a $C_{1-4}$-alkoxy radical, is, for example, a methoxy or ethoxy radical.

A particular value for $R^1$ when it is a $C_{1-4}$-alkoxy radical is, for example, a methoxy or ethoxy radical; and when it is a $C_{1-4}$-alkoxy radical bearing an N-morpholino or di-$C_{1-4}$-alkylamino radical, is, for example, a 2-(N-morpholino)ethoxy or 2-(N,N-dimethylamino)ethoxy radical.

A particular value for $R^6$ and $R^7$, when together they constitute a $C_{1-4}$-alkylenedioxy diradical, is, for example, a methylenedioxy, ethylenedioxy or isopropylidenedioxy diradical.

Particular combinations of $R^2$, $R^3$, $R^4$ and $R^5$ which are of special interest are when benzene ring A is, for example, a 2-fluoro-4-bromo-, 2-fluoro-4-chloro-, 2-fluoro-4-iodo-, 2-fluoro-4,5-dibromo-, 2-methoxy-4-chloro-, 4-bromo-, 4-iodo-, 3,5-dichloro-, 3-chloro-4-bromo-, 3,4-dichloro-, 3,4-dibromo- or a 3,5-dichloro-4-bromo-phenyl radical.

Particular combinations of $R^6$, $R^7$ and $R^8$ which are of special interest are, for example, when benzene ring B is unsubstituted or bears a 6-fluoro, 6-chloro, 6-methyl, 7-fluoro, 7-chloro, 7-methyl, 7-methoxy, 8-fluoro, 8-methyl or 8-ethoxy radical, or a 6,7-dichloro or 6,7-methylenedioxy diradical.

A particular base-addition salt of a compound of formula I wherein $R^1$ is a hydroxy radical is, for example, an alkali metal or alkaline earth metal salt, for example a sodium, potassium, calcium or magnesium salt, an aluminum or ammonium salt, or a salt of an organic base affording a pharmaceutically acceptable cation, for example a salt of triethanolamine.

A particular acid-addition salt of a compound of formula I wherein $R^1$ is a $C_{1-4}$-alkoxy radical bearing an N-morpholino or di-$C_{1-4}$-alkylamino radical is, for example, a hydrohalide, for example a hydrochloride or hydrobromide, or a sulphate.

Specific groups of compounds which are particularly preferred comprise those compounds of formula I wherein:
  (i) $R^1$ is a hydroxy radical;
  (ii) $R^2$ is a fluoro radical, $R^3$ and $R^5$ are hydrogen, and $R^4$ is a chloro, bromo or iodo radical;
  (iii) $R^3$ and $R^4$ are both independently chloro, bromo or iodo radicals, and $R^2$ and $R^5$ are hydrogen;
  (iv) $R^6$, $R^7$ and $R^8$ are hydrogen; or
  (v) X is oxygen;
and in each of the groups (i)–(v) the remainder of $R^1$, $R^2$, $R^3$, $R^4$, $R^5$, $R^6$, $R^7$, $R^8$ and X have any of the above defined values, or those defined in any other group; together with the pharmaceutically acceptable salts thereof, depending on the nature of $R^1$.

Specific compounds of the invention are described in the accompanying Examples and of these the following are preferred:
2-(2-fluoro-4-bromobenzyl)-1,2-dihydro-1-oxophthalazin-4-ylacetic acid, 2-(2-fluoro-4-iodobenzyl)-1,2-dihydro-1-oxophthalazin-4-ylacetic acid, and 2-(3-chloro-4-bromobenzyl)-1,2-dihydro-1-oxo-phthalazin-4-ylacetic acid; together with the pharmaceutically acceptable base-addition salts thereof.

The compounds of the invention may be manufactured by general procedures of organic chemistry well known in the art for the preparation of chemically analogous compounds. Such processes are provided as a further feature of this invention and are illustrated by the following, wherein $R^1$, $R^2$, $R^3$, $R^4$, $R^5$, $R^6$, $R^7$, $R^8$, X and benzene rings A and B have any of the meanings stated hereinabove unless otherwise stated:

(a) For a compound of formula I wherein X is oxygen, reacting a compound of the formula:

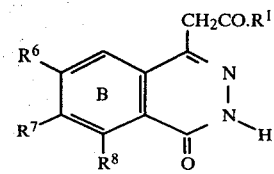

with a halide of the formula:

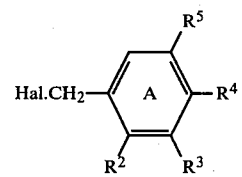

wherein Hal. is a chloro, bromo or iodo radical, in the presence of a suitable base.

The process is preferably carried out in a solvent or diluent, for example, ethanol, dimethylformamide, dimethyl sulphoxide or water, and is conveniently accelerated by heating in the range, for example, 40°–110° C.

A particularly suitable base is, for example, an alkali metal hydride, hydroxide or $C_{1-4}$-alkoxide, for example sodium or potassium hydride, hydroxide, methoxide or ethoxide; it being understood that when a hydride is used, a non aqueous solvent, for example dimethylformamide or dimethyl sulphoxide, is necessary, and when an alkoxide is used, a $C_{1-4}$-alkanol, for example methanol or ethanol, is preferably used as solvent.

It will be apparent that when a compound of formula III wherein $R^1$ is a hydroxy radical is used in the process, it is necessary for at least two molar equivalents of the base to be present, since the first molar equivalent reacts with the carboxylic acid radical of such a compound. In addition, for such a compound of formula III, it is preferable to use a hydroxylic solvent for the process in order that concomitant production of the corresponding ester is minimised.

(b) For a compound of formula I wherein $R^1$ is a hydroxy radical, hydrolysing an ester of the formula:

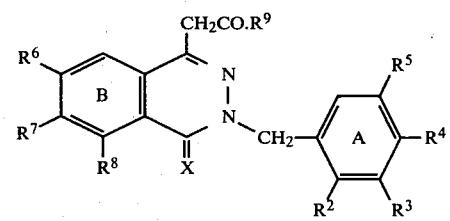

wherein $R^9$ is a $C_{1-4}$-alkoxy radical or a radical of the formula:

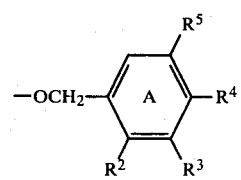

A particularly suitable value for a $C_{1-4}$-alkoxy radical is, for example, a methoxy or ethoxy radical and for a radical of formula VI, is any value for benzene ring A defined hereinbefore, for example an optionally substituted benzyl radical.

The hydrolysis may be carried out in the presence of acid or base, for example in the presence of a mineral acid, for example hydrochloric acid, or of an alkali metal hydroxide or carbonate, for example sodium or potassium hydroxide or carbonate. An alkali metal carbonate is preferred when benzene ring B bears a labile substituent, for example, an 8-fluoro radical. The hydrolysis is carried out in the presence of water and a solvent or diluent, for example, acetic acid, methanol, ethanol or dioxan, may also be present. The hydrolysis may be carried out at room temperature, for example at 18°–25° C., but is conveniently accelerated by heating, for example at 35°–110° C.

(c) For a compound of formula I wherein X is oxygen, reacting a compound of the formula:

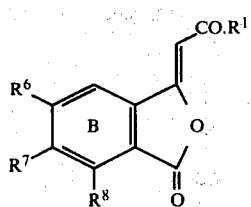

VII or a geometric isomer thereof, with a hydrazine of the formula:

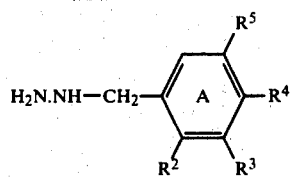

VIII

The process is preferably carried out in an aqueous diluent or solvent, for example aqueous dioxan, ethanol or dimethylformamide, and in the presence of a base, for example sodium or potassium hydrogen carbonate. The process is also conveniently carried out by heating at, for example, 40°–110° C.

(d) For a compound of formula I wherein X is oxygen and $R^1$ is a hydroxy or $C_{1-4}$-alkoxy radical, catalytically decomposing a diazoketone of the formula:

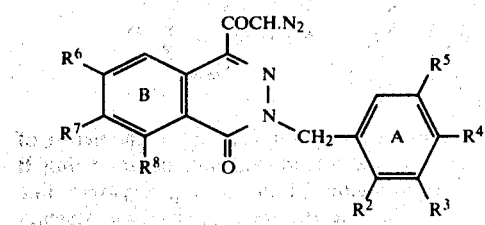

IX in the presence of a compound of the formula Q.H wherein Q is a hydroxy or a $C_{1-4}$-alkoxy radical, for example a methoxy or ethoxy radical.

The necessary catalyst may be provided by, for example, colloidal silver, or silver benzoate, and is preferably used in the presence of a base, for example, triethylamine, pyridine or s-collidine. The process is preferably carried out in the presence of a diluent or solvent, for example water, a $C_{1-4}$-alkanol, for example methanol or ethanol, tetrahydrofuran or dioxan, and is conveniently carried out using an excess of the compound of formula Q.H, optionally together with tetrahydrofuran or dioxan.

The process is conveniently accelerated by heating, for example by heating to a temperature in the range 40°–110° C.

(e) For a compound of formula I wherein $R^1$ is a hydroxy radical, decarboxylating a malonic acid of the formula:

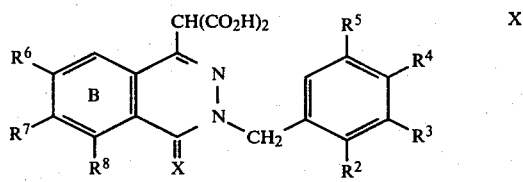

X

The decarboxylation may either be carried out by thermal means alone, for example by heating at a temperature in the range 50°–150° C. optionally in the presence of a solvent or diluent, for example ethylene glycol or diphenyl ether; or alternatively, by treatment with acid optionally in the presence of heat, for example by treating with sulphuric or hydrochloric acid at a temperature in the range 20°–150° C., conveniently in a solvent or diluent, for example, water, ethanol or acetic acid.

(f) For a compound of formula I wherein benzene ring B bears a $C_{1-4}$-alkoxy radical, reacting a compound of formula I wherein benzene ring B bears a halogeno radical, for example a fluoro radical, with an alkali metal $C_{1-4}$-alkoxide, for example sodium methoxide or ethoxide.

The reaction is preferably carried out in a solvent or diluent, for example, in an excess of the corresponding $C_{1-4}$-alkanol, for example methanol or ethanol, and may be accelerated by heating at, for example, 40°–110° C., or conveniently at the boiling point of the reaction mixture.

Whereafter, for a compound of formula I wherein $R^1$ is other than a hydroxy radical, the corresponding compound of formula I, wherein $R^1$ is a hydroxy radical (that is the corresponding acetic acid of formula I), or a reactive derivative thereof, for example the corresponding acid chloride, bromide or anhydride, is reacted using well known esterification procedures and conditions with the appropriate compound of the formula $R^{10}.H$, wherein $R^{10}$ has the same meaning as $R^1$ other than a hydroxy radical.

Whereafter, for a compound of formula I wherein X is sulphur, the corresponding oxo compound of formula I, wherein X is oxygen, is thiated using well known procedures and conditions, for example by reaction with phosphorus pentasulphide in boiling xylene or pyridine.

Both these well known procedures are illustrated in the accompanying Examples.

The starting materials may in general be prepared by standard procedures of heterocyclic chemistry well known in the art, for example as reviewed by N. R. Patel in "The Chemistry of Heterocyclic Compounds" Vol. 27, published by Interscience, New York. Such procedures are typified by those used for the preparation of the diazoketones of formula IX required for process (d) and shown in Scheme 1, in which the reagents used are as follows:

(i) n-Bu.Li, Et₂O or (MeOCH₂)₂, −10°–0° C.
(ii) diethyloxalate, 0°–5° C.

sponding acid after the alkylation and before step (vii) is carried out.

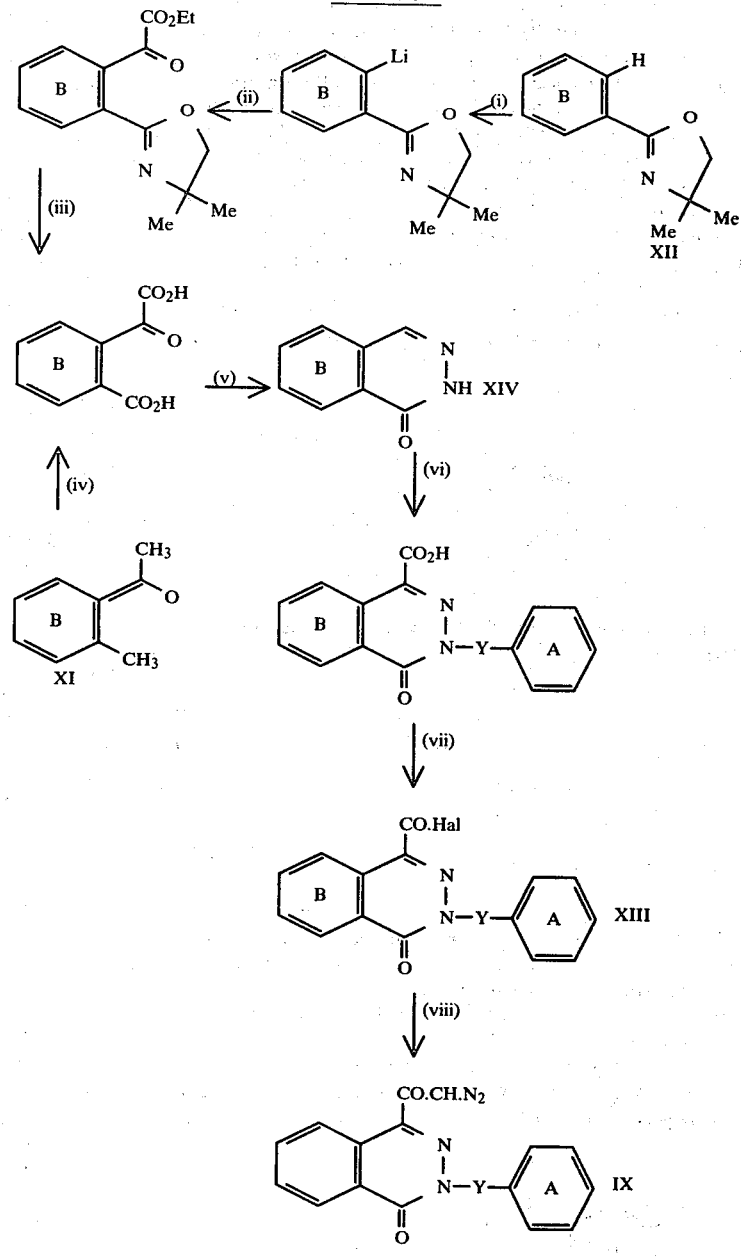

Scheme 1

(iii) H+H₂O/dioxan, 90°–100° C.
(iv) K₂CO₃/KMnO₄/H₂O, 100° C.
(v) H₂NNH₂.H₂O, 90°–100° C.
(vi) as process (a)
(vii) SO.(Hal.)₂, (Hal.=Cl or Br) or (COCl)₂
(viii) excess CH₂N₂/Et₂O;
and in which, for clarity, individual radicals R²–R⁸ are not shown. In many cases it is convenient to convert the acid of formula XIV to its methyl ester, for example by reaction of its sodium salt with methyl iodide in dimethyl formamide, before carrying out the alkylation with the benzyl halide [step (vi)]. This modification is described in Examples 8, 9 and 31–34 hereinafter and necessitates a conventional hydrolysis to the corre- It will be appreciated that depending on the nature of the substituents to be introduced into benzene ring B either the 2-acyltoluene XI or the 2-phenyloxazoline XII derivatives may be the most appropriate starting materials. Equally, it will be appreciated that it may be convenient to avoid the isolation and purification of several of the intermediates in Scheme 1, for example of the lithio and oxalato derivatives produced by steps (i) and (ii) respectively. Similarly, when carrying out process (d) hereinabove, it is convenient to prepare diazoketone IX in situ from acid halide XIII.

The starting materials of formula III for process (a) may be obtained by analogy with process (c), that is by reacting a compound of formula VII with hydrazine hydrate, and then, if a compound of formula III in which $R^1$ is other than a hydroxy radical is required, converting the phthalazin-4-ylacetic acid product as the free acid or acid chloride into the appropriate ester by conventional, known general procedures.

Some of the starting materials of formula VII may conveniently be obtained from the corresponding substituted phthalic anhydride of the formula:

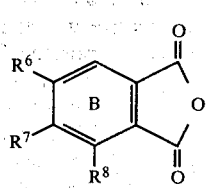  XV by condensation with acetic anhydride, for example in the presence of sodium or potassium acetate and in an excess of boiling acetic anhydride. However, they may all be obtained by a Wittig reaction between the appropriate phthalic anhydride of formula XV and (carbethoxymethylene)triphenylphosphorane in a suitable solvent, for example, 1,2-dimethoxyethane or tetrahydrofuran, the reaction conveniently accelerated by heating, for example, at the boiling point of the reaction mixture. It will be appreciated that in some cases the product from the Wittig reaction may be the geometric isomer of the formula:

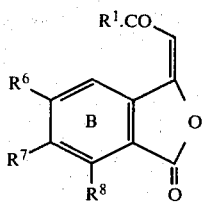  VIIa rather than that depicted in formula VII. Alternatively a mixture of both geometric isomers may be formed. Either isomer or a mixture thereof may be employed in process (c). It should also be noted that when $R^8$ and one of $R^7$ and $R^6$ are hydrogen the Wittig reaction produces positional isomers depending on which of the two carbonyl radicals of the phthalic anhydride XV reacts. When $R^8$ is other than hydrogen one positional isomer predominates i.e. that formed by reaction of the carbonyl radical furthest from $R^8$.

The malonic acid starting materials of formula X may be conveniently obtained by base catalysed hydrolysis of the corresponding diester of formula XVI, for example using aqueous ethanolic sodium hydroxide at 20°–100° C., followed by acidification at 20°–25° C. rather than at higher temperatures, which latter lead to decarboxylation in accordance with process (e) hereinabove. The necessary diester starting materials of formula XVI may themselves be obtained by reacting a dialkyl phthalidenemalonate of the formula XVII with the appropriate hydrazine of formula VIII:

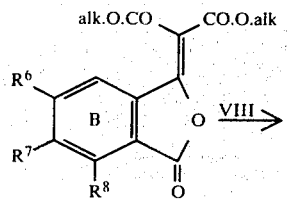  XVII

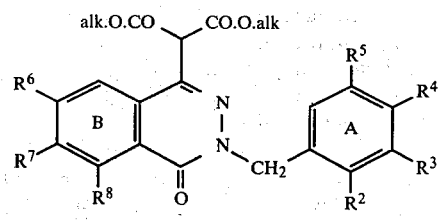  XVI using similar conditions to those described in connection with analogous process (c). The phthalidenemalonates of formula XVII may be obtained by reaction of a dialkyl malonate with the appropriate phthalic anhydride of formula XV, conveniently in the presence of acetic anhydride and a base, for example triethylamine.

The pharmaceutically acceptable salts as defined hereinbefore may be made by conventional procedures by reaction with the appropriate base or acid affording a pharmaceutically acceptable cation or anion respectively.

The property of inhibiting the enzyme aldose reductase may be demonstrated in the following standard laboratory test. Thus, rats are made diabetic by dosing with streptozotocin and are then dosed daily with the test compound for 5 days. The animals are then killed and the eye lenses and sciatic nerves are removed. After a standard work-up procedure the residual sorbitol levels in each tissue are determined by gas liquid chromatography after conversion to the poly trimethylsilyl derivatives. Inhibition of aldose reductase in vivo is then assessed by comparing the residual sorbitol levels in tissues from the dosed diabetic group of rats with those of an undosed group of diabetic rats and an undosed, normal group of rats.

Alternatively, a modified test may be used in which the streptozotocin induced diabetic rats are dosed daily with test compound for two days. After 2–4 hours from the final dose the animals are killed and the sciatic nerves are removed and assessed for residual sorbitol levels as described above.

Active compounds in either of these tests reduce residual sorbitol levels to levels which are similar to those of normal, undosed rats. However, in general the compounds of formula I produce significant inhibition of the enzyme aldose reductase at an oral dose of 100 mg./kg. or less. Thus, by way of illustration, 2-(2-fluoro-4-bromobenzyl)-1,2-dihydro-1-oxophthalazin-4-ylacetic acid produced a residual sorbitol level in the sciatic nerve of approximately 60% of that obtained in control undosed diabetic rats following oral dosing at 10 mg./kg. for 5 days. No overt toxic or other undesirable effects were detected with compounds of formula I at 100 mg./kg. in the above tests.

The property of inhibiting the enzyme aldose reductase may also be demonstrated in vitro. Thus, purified aldose reductase is isolated in known manner from bovine lenses. The percentage inhibition of this enzyme's ability in vitro to reduce aldoses to polyhydric alcohols, and particularly to reduce glucose to sorbitol, caused by a test compound is then determined using standard spectrophotometric methods. In this test those compounds of formula I wherein $R^1$ is a hydroxy radical shown significant inhibition of the enzyme aldose reductase at a concentration in the range $10^{-8}$ to $10^{-6}$ M or less. Thus, by way of illustration, 2-(2-fluoro-4-bromobenzyl)-1,2-dihydro-1-oxophthalazin-4-ylacetic acid has a $K_i$ of $2.0 \times 10^{-8}$ M.

When a compound of the invention is used to produce an effect on the enzyme aldose reductase in warm-blooded animals it may be administered primarily orally at a daily dose of 2 to 50 mg./kg., which is equivalent in man to a total daily dose in the range 20 to 750 mg. per man, given in divided doses if necessary.

The compounds of the invention may be administered in the form of pharmaceutical compositions and according to a further feature of the invention there is provided a pharmaceutical composition which comprises a compound of formula I, or a pharmaceutically acceptable salt thereof, together with a pharmaceutically acceptable diluent or carrier.

Especially preferred pharmaceutical compositions are those which are in a form suitable for oral administration, for example tablets, capsules, suspensions or solutions, which may be obtained by conventional methods and, if desired, may incorporate conventional diluents, carriers or other excipients. Other preferred compositions are those which are in a form suitable for parenteral administration, for example sterile injectable aqueous or non-aqueous solutions or suspensions, and for rectal administration, for example suppositories. Dosage forms will generally contain from 10 mg. to 250 mg. of a compound of formula I, or an equivalent amount of a pharmaceutically acceptable salt thereof, per dosage unit.

The compositions of the invention may also contain one or more agents which may have a useful effect in the treatment of diabetes or galactosemia, for example a hypoglycaemic agent such as tolbutamide.

Several of the compounds of the invention possess, in addition to aldose reductase inhibitory properties, anti-flammatory/analgesic properties of the type possessed by non-steroidal anti-inflammatory agents such as indomethacin, naproxen and ketoprofen. The compounds of the invention may therefore in addition be useful in the treatment of painful inflammatory joint diseases such as rheumatoid arthritis, osteoarthritis and ankylosing spondylitis. In this connection it is envisaged that they would be administered primarily orally at a daily dose in the range 10–50 mg./kg. The anti-inflammatory properties may be demonstrated in well known standard laboratory tests in rats. Thus, by way of example, 2-(2-fluoro-4-bromobenzyl)-1,2-dihydro-1-oxophthalazin-4-ylacetic acid and 2-(3-chloro-4-bromobenzyl)-1,2-dihydro-1-oxophthalazin-4-ylacetic acid both give rise to significant inhibition of carageenin induced oedema in the test developed by Winter et alia [*Proceedings of the Society of Experimental Biology* (New York), 1962, 111, 554] without any sign of overt toxicity.

The invention is illustrated by the following non-limiting Examples in which:

(i) all evaporations were carried out by rotary evaporation in vacuo unless otherwise stated;

(ii) all operations were performed at room temperature unless otherwise stated, room temperature being in the range 18°–26° C.;

(iii) petroleum ether (b.p. 60°–80° C.) is referred to as "petrol (60–80)", and other petroleum ether fractions accordingly;

(iv) melting points of acetic acids are associated with decomposition in many cases;

(v) all compounds of formula I and isolated intermediates were characterised on the basis of microanalysis and NMR and IR spectroscopy; and (vi) yields, where given are for illustration and do not necessarily represent the maximum attainable.

EXAMPLE 1

1,2-Dihydro-1-oxophthalazin-4-ylacetic acid (2.0 g.) was added to a solution of sodium hydroxide (0.9 g.) in methanol (50 ml.). A clear solution was obtained on slight warming, which was treated with 4-bromobenzyl bromide (2.6 g.). The mixture was then heated under reflux for 3 hours and then evaporated. The residue was treated with water (60 ml.) and the solution obtained was extracted with ether (3×60 ml.). The aqueous phase was then acidified to pH 2 with concentrated hydrochloric acid and the acid mixture extracted with ethyl acetate (150 ml.). The extracts were washed with water (50 ml.), dried (MgSO$_4$) and evaporated. The solid obtained was recrystallised from a 1:4 v/v mixture of ethyl acetate and petrol (60–80) to give 2-(4-bromobenzyl)-1,2-dihydro-1-oxophthalazin-4-ylacetic acid (0.6 g.), m.p. 179°–181° C.

EXAMPLE 2

A mixture of ethyl 1,2-dihydro-1-oxophthalazin-4-ylacetate (11.5 g.) and sodium hydride (2.7 g.; 50% w/w dispersion in mineral oil) in dimethylformamide (125 ml.) was stirred at 60° C. for 1 hour under nitrogen. The solution obtained was cooled to room temperature and then 4-bromo-3-chlorobenzyl bromide (15.0 g.) was added, and the mixture stirred at 60° C. for 2 hours. After cooling to 25° C. the reaction mixture was poured into water (500 ml.). The aqueous mixture obtained was extracted with ethyl acetate (400 ml.). The extracts were washed with water, dried (MgSO$_4$), and evaporated to give a solid, which was crystallised from propan-2-ol to yield ethyl 2-(3-chloro-4-bromobenzyl)-1,2-dihydro-1-oxophthalazin-4-ylacetate (7.3 g.), m.p. 142°–145° C.

EXAMPLES 3–4

Using a similar procedure to that described in Example 2, the following compounds of the formula:

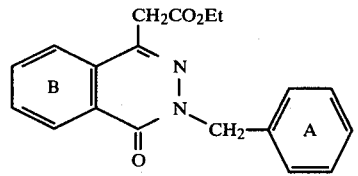

in which ring B is unsubstituted, were obtained from ethyl 1,2-dihydro-2-oxophthalazin-4-ylacetate and the appropriate bromide of the formula:

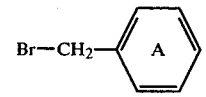

| Example | substituents on benzene ring A | yield (%) | m.p. (°C.) | recrystallisation solvent |
|---|---|---|---|---|
| 3 | *3,4-dichloro | 40 | 139–141 | i-PrOH |
| 4 | 2-fluoro-4-bromo | 60 | 114 | EtOH |

[*note: 3,4-dichlorobenzyl chloride used as starting material].

EXAMPLE 5

A solution of ethyl 2-(3-chloro-4-bromobenzyl)-1,2-dihydro-1-oxophthalazin-4-ylacetate (7.0 g.) in ethanol (70 ml.) containing potassium hydroxide (7.0 g.) was heated under reflux for 30 minutes. The solution was then poured into water (250 ml.) and the aqueous solution was extracted with ether (2×150 ml.). The aqueous phase was acidified to pH 2 with concentrated hydrochloric acid. The solid which was thus precipitated was separated, washed with water, dried in vacuo and then recrystallised from a 6:2:3 v/v mixture of toluene, propan-2-ol and petrol (60–80) to give 2-(3-chloro-4-bromobenzyl)-1,2-dihydro-1-oxophthalazin-4-ylacetic acid (3.9 g.), m.p. 186° C.

EXAMPLES 6–7

Using a similar procedure to that described in Example 5, the following compounds of the formula:

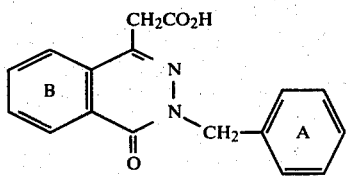

XX in which ring B is unsubstituted, were obtained by hydrolysis of the appropriate ethyl ester of formula (1):

| Example | substituents on benzene ring A | yield (%) | m.p. (°C.) | recrystallisation solvents |
|---|---|---|---|---|
| 6 | 3,4-dichloro | 60 | 175–176 | toluene-i-PrOH |
| 7 | 2-fluoro-4-bromo | 64 | *184–185 | methanol |

*Note: This compound can crystallise in polymorphic forms, that is a form m.p. 184–185° C. (from methanol containing some water) and a form m.p. 180–182° C. (from two crystallisations from dry methanol).

EXAMPLE 8

A stirred mixture of 2-(3,4-dichlorobenzyl)-7-methoxy-1,2-dihydro-1-oxophthalazin-4-ylcarboxylic acid (1.9 g.) in thionyl chloride (10 ml.) containing dimethylformamide (0.1 ml.) was heated under reflux for 3 hours. The solution obtained was then evaporated. The residue was dissolved in dry toluene and the solution evaporated. This procedure was carried out three times to give 2-(3,4-dichlorobenzyl)-7-methoxy-1,2-dihydro-1-oxophthalazin-4-ylcarboxylic acid chloride in essentially quantitative yield as a solid, having a satisfactory IR spectrum.

A solution of the above acid chloride in dry tetrahydrofuran (50 ml.) was added dropwise to a stirred solution of diazomethane in dry ether (200 ml.) cooled to 0° C. [obtained as described by J A Moore (*Organic Syntheses* 1961, 41, 16) from bis-(N-methyl-N-nitroso)-terephthalamide (10 g.)]. After the addition was complete, the mixture was further stirred and allowed to warm up to room temperature during 2 hours. The mixture was then separated by filtration. The residue obtained was washed with dry tetrahydrofuran (20 ml.) and the combined washings and filtrate were evaporated to give 2-(3,4-dichlorobenzyl)-4-(α-diazo)acetyl-7-methoxy-1,2-dihydro-1-oxophthalazine, as a solid which was used without purification or characterisation.

A solution of silver benzoate (0.2 g.) in triethylamine (1 ml.) was added slowly dropwise to a solution of the above 4-(α-diazo)acetyl derivative in absolute ethanol (50 ml.) and tetrahydrofuran (30 ml.) heated under reflux. (After each addition, effervescence occurred and this was allowed to subside before further solution was added.) After the addition was complete, the reaction mixture was further stirred and heated under reflux for 30 minutes and then filtered whilst hot. The filtrate was evaporated and the residue obtained dissolved in ethyl acetate (200 ml.). The ethyl acetate solution was washed with water (3×100 ml.), dried (MgSO$_4$) and evaporated. The residue was purified by chromatography on silica (100 g.) using an increasing concentration of ethyl acetate in toluene as the eluant. There was thus obtained from the appropriate fractions [as judged by thin layer chromatography (TLC) on silica plates using ethyl acetate-toluene (1:3 v/v) as eluant] ethyl 2-(3,4-dichlorobenzyl)-7-methoxy-1,2-dihydro-1-oxophthalazin-4-ylacetate (0.9 g.), m.p. 129°–130° C.

The necessary starting material was obtained as follows:

(a) A mixture of 7-methoxy-1,2-dihydro-1-oxophthalazin-4-ylcarboxylic acid (10.0 g.), sodium hydrogen carbonate (15.0 g.) and methyl iodide (15.0 ml.) in dry dimethylformamide (200 ml.) was stirred at room temperature for 16 hours. The mixture was then poured into water (600 ml.). The precipitated solid was separated, washed first with water then cold methanol, and then recrystallised from methanol to give methyl 7-methoxy-1,2-dihydro-1-oxophthalazin-4-ylcarboxylate (8.6 g.), m.p. 222°–225° C.

(b) A solution of the methyl ester (8.29 g.), obtained in (a) above, in dry dimethylformamide (200 ml.) was treated with sodium hydride (1.75 g., 50% w/w dispersion in mineral oil). The mixture was stirred at 60° C. for one hour, cooled to room temperature, and 3,4-dichlorobenzyl chloride (7.0 g.) added. The subsequent mixture was stirred at room temperature for 2 hours and then poured into water (600 ml.). The solid which formed was separated, washed with water, dried in vacuo and then recrystallised from a 1:3 v/v mixture of propan-2-ol and petrol (60–80) to give methyl 2-(3,4-dichlorobenzyl)-7-methoxy-1,2-dihydro-1-oxophthalazin-4-ylcarboxylate (9.0 g.), m.p. 144°–146° C.

(c) A solution of the methyl ester (9.0 g.), obtained in (b) above, in ethanol (100 ml.) and water (100 ml.) containing potassium hydroxide (10.0 g.) was heated under reflux for 4 hours. The solution obtained was then diluted with water (200 ml.) and acidified to pH 2 with concentrated hydrochloric acid. The solid which was thus deposited was separated, washed with water, dried in vacuo and recrystallised from a 1:1 v/v mixture of propan-2-ol and dimethylformamide to give 2-(3,4-dichlorobenzyl)-7-methoxy-1,2-dihydro-1-oxophthalazin-4-ylcarboxylic acid (6.1 g.), m.p. 238°–240° C. [Note: 7-methoxy-1,2-dihydro-1-oxophthalazin-4-ylcarboxylic acid was obtained as a solid, m.p. 229°–230° C., by the procedure of Vaughan et alia (*J. Amer. Chem. Soc.* 1946, 68, 1314)].

EXAMPLE 9

Using a similar procedure to that described in Example 8, but starting from 2-(3,4-dichlorobenzyl)-7-chloro-1,2-dihydro-1-oxophthalazin-4-ylcarboxylic acid (A) there was obtained in 8% yield, ethyl 2-(3,4-dichlorobenzyl)-7-chloro-1,2-dihydro-1-oxophthalazin- 4-ylacetate, as a solid having a satisfactory NMR spectrum.

The necessary starting carboxylic acid derivative (A) was obtained using a similar procedure (a)–(c) to that described for the starting material in Example 8, but starting from 7-chloro-1,2-dihydro-1-oxophthalazin-4-ylcarboxylic acid (B). The necessary intermediates had the following melting points:

from step (a): methyl 7-chloro-1,2-dihydro-1-oxophthalazin-4-ylcarboxylate, m.p. 255°–257° C. (recrystallised from 2:1 v/v methanol:dimethylformamide);

from step (b): methyl 2-(3,4-dichlorobenzyl)-7-chloro-1,2-dihydro-1-oxophthalazin-4-ylcarboxylate, m.p. 178°–180° C. [recrystallised from 1:3 v/v propan-2-ol: petrol (60–80)];

from step (c): 2-(3,4-dichlorobenzyl)-7-chloro-1,2-dihydro-1-oxophthalazin-4-ylcarboxylic acid, m.p. 260°–262° C. (recrystallized from 1:1 v/v methanol: dimethylformamide).

[Note: carboxylic acid (B) was obtained as a solid, m.p. 241°–243° C., by a similar procedure to that of Vaughan et alia (*J. Amer. Chem. Soc.* 1946, 68, 1314), but starting from 4-chloro-2-methylacetophenone].

EXAMPLES 10–11

Using a similar procedure to that described in Example 5, but starting from the appropriate ethyl ester, the following acids were obtained:

(Example 10): 2-(3,4-dichlorobenzyl)-7-methoxy-1,2-dihydro-1-oxophthalazin-4-ylacetic acid, m.p. 198°–200° C. (recrystallised from propan-2-ol); yield 50%; (Example 11): 2-(3,4-dichlorobenzyl)-7-chloro-1,2-dihydro-1-oxophthalazin-4-ylacetic acid, m.p. 203°–205° C. [recrystallised from 1:1 v/v propan-2-ol: petrol (60–80)]; yield 43%.

EXAMPLES 12–13

Using a similar procedure to that described in Example 2, there were obtained using the appropriate benzyl bromide or chloride, the following esters:

(Example 12): ethyl 2-(2-fluoro-4-chlorobenzyl)-1,2-dihydro-1-oxophthalazin-4-ylacetate, m.p. 102° C. [recrystallised from petrol (60–80), then from ethanol]; yield 45%;

(Example 13): ethyl 2-(2-fluoro-4-iodobenzyl)-1,2-dihydro-1-oxophthalazin-4-ylacetate, m.p. 113° C. [recrystallised from petrol (60–80); yield 50%].

EXAMPLES 14–16

Using a similar procedure to that described in Example 5, but starting with the appropriate ethyl ester, there were obtained the following acids:

(Example 14): 2-(2-fluoro-4-chlorobenzyl)-1,2-dihydro-1-oxophthalazin-4-ylacetic acid, m.p. 193°–194° C. (recrystallised from 3:1 v/v ethanol:water); yield 63%;

(Example 15): 2-(2-fluoro-4-iodobenzyl)-1,2-dihydro-1-oxophthalazin-4-ylacetic acid, m.p. 189° C. (recrystallised from 3:1 v/v ethanol:water); yield 55%;

(Example 16)*: 2-(3-chloro-4-bromobenzyl)-1,2-dihydro-1-thioxophthalazin-4-ylacetic acid, m.p. 197°–199° C. (recrystallised from propan-2-ol); yield 25%.

[*Hydrolysis carried out with aqueous methanolic sodium hydroxide solution, under reflux for 10 minutes.]

EXAMPLE 17

A mixture of ethyl 2-(3-chloro-4-bromobenzyl)-1,2-dihydro-1-oxophthalazin-4-ylacetate (1.8 g.) and phosphorus pentasulphide (2.5 g.) in xylene (100 ml.) was stirred and heated under reflux for 1 hour. The reaction solution was then cooled to room temperature, ethyl acetate (25 ml.) was added and the mixture was filtered through chromatographic silica (20 g.), the subsequent filtrate was evaporated and the residual solid obtained was recrystallised from ethanol to give ethyl 2-(3-chloro-4-bromobenzyl)-1,2-dihydro-1-thioxophthalazin-4-ylacetate (1.1 g.), m.p. 124°–126° C.

EXAMPLE 18

3-Chloro-4-bromobenzylhydrazine (2.5 g.) was added to a stirred mixture of 3-oxo-Δ1,α-phthalanacetic acid (also known as phthalideneacetic acid (1.92 g.) and sodium hydrogen carbonate (2.0 g.) in dioxan (50 ml.) and water (25 ml.). The mixture was then heated under reflux for 3 hours, cooled to room temperature and poured into water (200 ml.). The aqueous solution was extracted with ether (3 × 100 ml.) and the aqueous phase was acidified with concentrated hydrochloric acid to pH 2. The solid which deposited was collected, washed well with water, dried in vacuo, and then recrystallised twice from a mixture of toluene isopropanol and petrol (60–80) (6:2:3 v/v/v) to give 2-(3-chloro-4-bromobenzyl)-1,2-dihydro-1-oxophthalazin-4-ylacetic acid (0.23 g.), m.p. 184°–186° C.

EXAMPLES 19–23

Using a similar procedure to that described in Example 2 but using the appropriate benzyl bromide of formula XIX there were obtained the following compounds of formula XVIII in which ring B is unsubstituted:

| Example | substituents on benzene ring A | yield (%) | m.p. (°C.) | recrystallisation solvent(s) |
|---------|-------------------------------|-----------|------------|------------------------------|
| 19 | 3,4-dibromo | 44 | 140–142 | i-PrOH |
| 20 | 2-fluoro-4,5-dibromo | 21 | 129–130 | EtOAc |
| 21 | 3,5-dichloro | 36 | 100–101 | EtOAc |
| 22 | 3,5-dichloro-4-bromo | 19 | 146–147 | EtOH |
| 23 | 2-methoxy-4-chloro | 22 | 138 | i-PrOH |
| 24 | 4-iodo | 43 | 106–107 | i-PrOH/petrol 1:3 (60–80) |

EXAMPLES 25–26

Ethyl 4-methyl-3-oxo-Δ1α-phthalanacetate (2.29 g.) was heated and stirred under reflux in toluene (200 ml.) during the dropwise addition of a solution of 3,4-dichlorobenzylhydrazine (1.9 g.) in toluene (50 ml.). The mixture was further heated under reflux for 3 hours, cooled and evaporated. The solid residue was recrystallised from 1:2 v/v isopropanol and petrol (60–80) to give ethyl 2-(3,4-dichlorobenzyl)-8-methyl-1,2-dihydro-1-oxophthalazin-4-ylacetate (Example 25) (1.4 g.), m.p. 134°–137° C.

In a similar manner, but starting from ethyl 4-fluoro-3-oxo-Δ1α-phthalanacetate, there was obtained ethyl 2-(3,4-dichlorobenzyl)-8-fluoro-1,2-dihydro-]-oxophthalazin-4-ylacetate (Example 26), m.p. 177°–178° C. [recrystallised from 1:2 v/v isopropanol/petrol (60–80)], in 37% yield.

Similarly, starting from a 1:1 mixture of 5-methyl- and 6-methyl-3-oxo-Δ1α-phthalanacetate, there was obtained a 1:1 mixture of ethyl 6-methyl- and 7-methyl-2-(3,4-dichlorobenzyl)-1,2-dihydro-1-oxophthalazin-4- ylacetate (Example 27), m.p. 120°–122° C. (recrystallisation from isopropanol) in 33% yield.

The required starting materials were obtained as follows:

A solution of 3-fluorophthalic anhydride (7.35 g.) and (carbethoxymethylene)triphenylphosphorane (17.5 g.) in dry 1,2-dimethoxyethane (200 ml.) was stirred and heated under reflux in an atmosphere of nitrogen for 16 hours. The solvent was then evaporated and the residue adsorbed onto chromatographic silica gel (20 g.). This silica gel was then added to the top of a column of the same silica gel (300 g.) and the column was eluted with toluene. The eluate was monitored by TLC (SiO$_2$ gel: eluant 9:1 v/v toluene/ethyl acetate) and the first fractions containing UV visible material were combined and evaporated. The residual solid obtained was recrystallized from isopropanol to give ethyl 4-fluoro-3-oxo-Δ1α-phthalanacetate (2.3 g.), m.p. 101°–103° C., required for Example 26.

In a similar manner, ethyl 4-methyl-3-oxo Δ,1α-phthalanacetate (required for Example 25) was obtained as a solid, m.p. 84°–86° C. in 56% yield after recrystallisation from isopropanol, starting from 3-methylphthalic anhydride.

Similarly, the 1:1 mixture of ethyl 5-methyl- and 6-methyl-3-oxo-Δ,1α-phthalanacetate (required for Example 27) was obtained in 40% yield as a solid, m.p. 84°–86° C. (recrystallised from isopropanol), starting from 4-methylphthalic anhydride.

EXAMPLES 28–30

Using a similar procedure to that described in Example 2 the following compounds were obtained from the appropriate substituted 1,2-dihydro-1-oxophthalazin-4-ylacetate and 2-fluoro-4-bromobenzylhydrazine:

Example 28: ethyl 2-(2-fluoro-4-bromobenzyl)-8-fluoro-1,2-dihydro-1-oxophthalazin-4-ylacetate, m.p. 128°–130° C. [recrystallised from 1:3 v/v isopropanol/petrol (60–80)] in 36% yield;

Example 29: ethyl 2-(2-fluoro-4-bromobenzyl)-8-methyl-1,2-dihydro-1-oxophthalazin-4-ylacetate, m.p. 120°–122° C. [recrystallised from 1:3 v/v isopropanol/petrol (60–80)] in 43% yield; and Example 30: ethyl 2-(2-fluoro-4-bromobenzyl)-6,7-methylenedioxy-1,2-dihydro-1-oxophthalazin-4-ylacetate, m.p. 163°–165° C. (recrystallised from ethyl acetate) in 56% yield.

The necessary starting materials were obtained in the following manner:

(i) Ethyl 8-methyl-1,2-dihydro-1-oxophthalazin-4-ylacetate (for Example 29)

A solution of ethyl 4-methyl-3-oxo-Δ1α-phthalanacetate (3.5 g.) in ethanol (100 ml.) was stirred and heated under reflux during the dropwise addition of hydrazine hydrate (15 ml. of a 1 M-solution in ethanol). After the addition was complete, the mixture was further stirred and heated under reflux for 3 hours and then allowed to cool to room temperature. The solid which was deposited was collected and washed well with petrol (60–80), and recrystallised from isopropanol/petrol (60–80) to give ethyl 8-methyl-1,2-dihydro-1-oxophthalazin-4-ylacetate (1.0 g.), m.p. 197°–199° C.

(ii) Ethyl 8-fluoro-1,2-dihydro-1-oxophthalazin-4-ylacetate (for Example 28)

This ester was obtained as a solid, m.p. 207°–210° C. (recrystallised from ethyl acetate) in 51% yield from ethyl 4-fluoro-3-oxo-Δ,1α-phthalanacetate and hydrazine hydrate, using the procedure described in (i) above.

(iii) Ethyl 6,7-methylenedioxy-1,2-dihydro-1-oxophthalazin-4-ylacetate (for Example 30)

This ester was obtained as a solid, m.p. 226°–228° C. in 70% yield from ethyl 5,6-methylenedioxy-3-oxo-Δ,1α-phthalanacetate (A) and hydrazine hydrate. The phthalanacetate (A) was itself obtained as a solid, m.p. 189°–191° C. (recrystallised from ethanol) in 64% yield from 4,5-methylenedioxyphthalic anhydride using an analogous procedure to that described for the corresponding intermediates in Examples 25–27. [This procedure is based on that of Knight and Porter, *Tetrahedron Letters*, 1977, 4543–4547].

EXAMPLES 31–34

Using an analogous procedure to that described in Example 8 the following esters of the formula XVIII were obtained from the appropriate starting materials:

| Example | Substituents on ring B | Substituents on ring A | Yield (%) | m.p. (°C.) | recrystallisation solvent(s) |
|---|---|---|---|---|---|
| 31 | 7-fluoro | 3,4-dichloro | 26 | 160–162 | i-PrOH |
| 32 | 6,7-dichloro | 3,4-dichloro | 70* | 204–205 | CHCl$_3$/EtOAc (1:2) |
| 33 | 6-chloro | 3,4-dichloro | 10 | 143–146 | EtOH |
| 34 | 6-fluoro | 2-fluoro-4-bromo | 60* | 121–123 | EtOH |

*Note: Diazomethane generated from bis(N—methyl—N—nitroso)terephthalamide by the improved procedure of Moore and Reed (Organic Syntheses, Collected Vol. 5, pp.351-355).

The necessary starting phthalazin-4-yl-carboxylic acids may be obtained as follows:

(i) 2-(3,4-dichlorobenzyl)-7-fluoro-1,2-dihydro-1-oxophthalazin-4-ylcarboxylic acid 7-Fluoro-1,2-dihydro-1-oxophthalazin-4-ylcarboxylic acid (obtained as a solid, m.p. 241°–243° C. in 52% yield by a similar procedure to that of Vaughan et alia, *J. Amer. Chem. Soc.* 1946, 68, 1314) was converted to its sodium salt and reacted with iodomethane by the procedure described in part (a) of Example 8 to give the corresponding methyl ester as a solid, m.p. 234°–237° C. [recrystallised from 3:1 v/v methanol/dimethylformamide (DMF)] in 68% yield. This ester was then alkylated with 3,4-dichlorobenzyl chloride by the procedure described in part (b) of Example 8 to give methyl 2-(3,4-dichlorobenzyl)-7-fluoro-1,2-dihydro-1-oxophthalazin-4-ylcarboxylate, m.p. 147°–149° C. [recrystallised from 1:1 v/v toluene/petrol (60–80)] in 68% yield. This ester was then hydrolysed using a mixture of aqueous potassium carbonate and dioxan using the procedure of Example 36 hereinafter to give 2-(3,4-dichlorobenzyl)-7-fluoro-1-2-dihydro-1-oxophthalazin-4-ylcarboxylic acid as a solid, m.p. 222°–224° C. (recrystallised from isopropanol) in 87% yield.

(ii)
2-(3,4-dichlorobenzyl)-6,7-dichloro-1,2-dihydro-1-oxophthalazin-4-ylcarboxylic acid This acid was obtained in an analogous manner to that in part (i) above, and the relevant intermediates, melting points, solvents and yields were as follows:
6,7-dichloro-1,2-dihydro-1-oxophthalazin-4-ylcarboxylic acid: m.p. 294°–296° C., (recrystallised from DMF), yield 42%; corresponding methyl ester: m.p. 234°–236° C. (recrystallised from DMF), yield 51%;
methyl 2-(3,4-dichlorobenzyl)-6,7-dichloro-1,2-dihydro-1-oxophthalazin-4-ylcarboxylate: m.p. 155°–156° C. (recrystallised from DMF), yield 85%;
2-(3,4-dichlorobenzyl)-6,7-dichloro-1,2-dihydro-1-oxophthalazin-4-ylcarboxylic acid: m.p. 240°–242° C. (recrystallised from ethanol), yield 62%.

(iii)
2-(3,4-dichlorobenzyl)-6-chloro-1,2-dihydro-1-oxophthalazin-4-ylcarboxylic acid A solution of butyl lithium in hexane (165 ml. of a 1.6 M solution) was added slowly to a stirred solution of 2-(4-chlorophenyl)-4,4-dimethyl-2-oxazoline (50.0 g.; prepared by the procedure of Meyers et alia, *J. Org. Chem.*, 1974, 39, 2787) in sodium dried ether (600 ml.) maintained at −5° to 0° C. and under an atmosphere of dry argon. Stirring was continued at this temperature for 30 minutes after the addition was complete and then the solution was added slowly to a stirred solution of dry diethyl oxalate (326 ml.) in ether (500 ml.) maintained at 0° C. Air and water were excluded during the transfer by the use of an atmosphere of dry argon. The reaction mixture was further stirred after the addition was complete and was allowed to warm up to room temperature during 1 hour. The ethereal mixture was then washed with water (2×150 ml.), dried (MgSO$_4$) and evaporated under reduced pressure (10 mm Hg.) until all excess diethyl oxalate was removed. The residue was dissolved in dioxan (500 ml.) and the solution added to 5 N hydrochloric acid (500 ml.). The mixture was heated under reflux for 18 hours, evaporated to half volume and the residual solution filtered. The filtrate was adjusted to pH 8 by addition of hydrazine hydrate and the solution heated at 90° C. for 30 minutes, and then acidified to pH 4 with concentrated hydrochloric acid. The mixture was cooled and the solid which separated was collected by filtration, washed with water (2×500 ml.) and dried in vacuo over phosphorus pentoxide to give 6-chloro-1,2-dihydro-1-oxophthalazin-4-ylcarboxylic acid (21.0 g.).

This acid was suspended in DMF (250 ml.) and the mixture treated with sodium hydrogen carbonate (21.0 g.) and iodomethane (40 ml.). The combined mixture was stirred overnight and then diluted with water (250 ml.). The solid which deposited was collected, washed with water (2×200 ml.) and recrystallised from 2:1 v/v isopropanol/DMF to give methyl 6-chloro-1,2-dihydro-1-oxophthalazin-4-ylcarboxylate (17.0 g.), m.p. 248°–250° C.

This ester was then reacted with 3,4-dichlorobenzyl chloride in an analogous manner to that described in part (i) and (ii) above. There was then obtained methyl 2-(3,4-dichlorobenzyl)-6-chloro-1,2-dihydro-1-oxophthalazin-4-ylcarboxylate, m.p. 168°–170° C. (recrystallised from toluene) in 45% yield. This ester was then hydrolysed as described in part (i) above to give 2-(3,4-dichlorobenzyl)-6-chloro-1,2-dihydro-1-oxophthalazin-4-ylcarboxylic acid, m.p. 222°–223° C. (recrystallised from ethanol) in 60% yield.

(iv)
2-(2-fluoro-4-bromobenzyl)-6-fluoro-1,2-dihydro-1-oxophthalazin-4-ylcarboxylic acid This acid was obtained in an analogous manner to that in part (iii) above, and the relevant intermediates, melting points, solvents and yields are as follows:
methyl 6-fluoro-1,2-dihydro-1-oxophthalazin-4-ylcarboxylate: m.p. 221°–223° C. (recrystallised from 2:1 v/v methanol/DMF), yield 15%;
methyl 2-(2-fluoro-4-bromobenzyl)-6-fluoro-1,2-dihydro-1-oxophthalazin-4-ylcarboxylate: m.p. 131°–134° C. (recrystallised from methanol), yield 51%;
2-(2-fluoro-4-bromobenzyl)-6-fluoro-1,2-dihydro-1-oxophthalazin-4-ylcarboxylic acid: m.p. 210°–211° C., (recrystallised from isopropanol), yield 70%.

EXAMPLE 35

Using a similar procedure to that described in Example 17, there was obtained ethyl 2-(2-fluoro-4-bromobenzyl)-1,2-dihydro-1-thioxophthalazin-4-ylacetate, m.p. 97°–99° C. (recrystallised from ethanol) in 22% yield by thiation of ethyl 2-(2-fluoro-4-bromobenzyl)-1,2-dihydro-1-oxophthalazin-4-ylacetate.

EXAMPLES 36–39

A mixture of potassium carbonate (1.5 g.), water (16 ml.), dioxan (50 ml.) and ethyl 2-(2-fluoro-4-bromobenzyl)-8-fluoro-1,2-dihydro-1-oxophthalazin-4-ylacetate (1.0 g.) was heated under reflux for 24 hours, and then evaporated. The residue was dissolved in water (100 ml.) and the solution washed with ether (2×100 ml.). The aqueous phase was acidified to pH 2 by addition of concentrated hydrochloric acid. The solid which formed was collected by filtration, washed with water, and recrystallised from a 7:1:5 v/v/v mixture of toluene/isopropanol/petrol (60–80) to give 2-(2-fluoro-4-bromobenzyl)-8-fluoro-1,2-dihydro-1-oxophthalazin-4-ylacetic acid (Example 36) (0.5 g.), m.p. 173°–175° C.

Using an analogous procedure, and starting from the appropriate ethyl esters, the following acetic acid derivatives were obtained:
Example 37: 2-(3,4-dichlorobenzyl)-7-fluoro-1,2-dihydro-1-oxophthalazin-4-ylacetic acid, m.p. 201°–202° C. (recrystallised from 1:2 v/v ethyl acetate/petol (60–80), yield 90%;
Example 38: 2-(3,4-dichlorobenzyl)-6,7-dichloro-1,2-dihydro-1-oxophthalazin-4-ylacetic acid, m.p. 204°–205° C. (recrystallised from 5:1 v/v methanol/DMF), yield 76%;
Example 39: 2-(3,4-dichlorobenzyl)-6-chloro-1,2-dihydro-1-oxophthalazin-4-ylacetic acid, m.p. 208°–209° C. (recrystallised from isopropanol), yield 55%.

EXAMPLES 40–52

Using a similar procedure to that described in Example 5 the following acetic acid derivatives of formula XX were obtained by hydrolysis of the corresponding ethyl esters with potassium hydroxide:

| Example | Substituent on ring B | Substituents on ring A | Yield (%) | melting point (°C.) | recrystallisation solvent(s) |
|---|---|---|---|---|---|
| 40 | none | 4-iodo | 64 | 178-180 | i-PrOH/petrol (60-80) (1:2) |
| 41 | none | 3,4-dibromo | 61 | 187-189 | i-PrOH |
| 42 | none | 2-fluoro-4,5-dibromo | 71 | 184-186 | i-PrOH |
| 43 | none | 3,5-dichloro-4-bromo | 60 | 219-220 | i-PrOH |
| 44 | none | 2-methoxy-4-chloro | 55 | 183-184 | i-PrOH |
| 45 | 8-fluoro | 3,4-dichloro | 68 | 143-145 | EtOAc/toluene |
| 46 | 6-methyl* + 7-methyl | 3,4-dichloro 3,4-dichloro | 43 | 182-184 | i-PrOH |
| 47 | 8-methyl | 2-fluoro-4-bromo | 37 | 195-197 | i-PrOH/petrol (60-80) (1:2) |
| 48 | 8-methyl | 3,4-dichloro | 44 | 203-205 | i-PrOH/petrol (60-80) (1:2) |
| 49 | 6,7-methylenedioxy | 2-fluoro-4-bromo | 70 | 209-210 | i-PrOH |
| 50 | 6-fluoro | 2-fluoro-4-bromo | 72 | 187-188 | i-PrOH |
| 51 | 8-ethoxy** | 3,4-dichloro | 65 | 204-206 | i-PrOH |

*1:2 mixture of 6-methyl and 7-methyl derivatives.
**exo-tautomer by NMR.

In a similar manner, 2-(2-fluoro-4-bromobenzyl)-1,2-dihydro-1-thioxophthalazin-4-ylacetic acid (Example 52) was obtained as a solid, m.p. 194°-196° C. (recrystallised from methanol) in 30% yield by hydrolysis of the corresponding ethyl ester with aqueous methanolic sodium hydroxide solution.

EXAMPLE 53

Ethyl 2-(3,4-dichlorobenzyl)-8-fluoro-1,2-dihydro-1-oxophthalazin-4-ylacetate (1.8 g.) was added to a solution of sodium (1.5 g.) in dry ethanol (150 ml.). The solution obtained was heated under reflux for 3 hours and then evaporated. Water (100 ml.) was added to the residue and the solid obtained was collected by filtration and dried to give ethyl 2(3,4-dichlorobenzyl)-8-ethoxy-1,2-dihydro-1-oxophthalazin-4-ylacetate (0.5 g.).

EXAMPLE 54

Acetyl chloride (10 ml.) was added to stirred methanol (150 ml.) to give a solution of hydrogen chloride in methanol and methyl acetate. 2-(2-Fluoro-4-bromobenzyl)-1,2-dihydro-1-oxophthalazin-4-ylacetic acid (2.1 g.) was added to this solution and the mixture was heated under reflux for 18 hours, and then cooled to room temperature. The solid which crystallised out was separated by filtration and recrystallised from methanol to give methyl 2-(2-fluoro-4-bromobenzyl)-1,2-dihydro-1-oxophthalazin-4-ylacetate (1.4 g.), m.p. 151°-153° C.

EXAMPLES 55-57

A solution of 2-(2-fluoro-4-bromobenzyl)-1,2-dihydro-1-oxophthalazin-4-ylacetyl chloride (1.65 g.) [prepared in situ by heating the corresponding acid (1.6 g.) under reflux with oxalyl chloride (2.5 ml.) and DMF (0.1 ml.) in dry benzene (30 ml.) for 3 hours and then exaporating the mixture azeotropically with dry toluene] was prepared in methylene chloride (20 ml.). This solution was then added dropwise to an ice-cooled stirred solution of N-(2-hydroxyethyl)morpholine (1.5 g.) and triethylamine (2 ml.) in methylene chloride (100 ml.). The stirred mixture was then allowed to attain room temperature during 18 hours, was next washed with water (2×100 ml.), and then extracted with 2 N-hydrochloric acid (2×50 ml.). The acid extracts were washed with ether (2×100 ml.) and the ethereal extracts discarded. The aqueous phase was basified to pH 10 with potassium carbonate and then extracted with ethyl acetate (2×100 ml.). These extracts were washed with water (2×100 ml.), dried (MgSO₄) and evaporated to give a solid which was crystallised from petrol (80-100) to yield 2-(N-morpholino)ethyl 2-(2-fluoro-4-bromobenzyl)-1,2-dihydro-1-oxophthalazin-4-ylacetate (Example 55) (0.5 g.), m.p. 99°-100° C.

In a similar manner starting with 2-(N,N-dimethylamino)ethanol and benzyl alcohol respectively, there were obtained:

Example 56: 2-(N,N-dimethylamino)ethyl 2-(2-fluoro-4-bromobenzyl)-1,2-dihydro-1-oxophthalazin-4-ylacetate, m.p. 75°-77° C. [recrystallised from petrol (80-100)] in 16% yield; and Example 57: benzyl 2-(2-fluoro-4-bromobenzyl)-1,2-dihydro-1-oxophthalazin-4-ylacetate, m.p. 105°-107° C. [recrystallised from petrol (80-100)] in 50% yield; this ester was isolated from the initial CH₂Cl₂ phase.

EXAMPLE 58

A solution of sodium methoxide (25 ml. of a 1.0 M solution in methanol) was added to a solution of 2-(2-fluoro-4-bromobenzyl)-1,2-dihydro-1-oxophthalazin-4-ylacetic acid (9.87 g.) in methanol (300 ml.) and the mixture heated to its boiling point. Methanol was then allowed to boil off until the volume of the mixture was approximately 100 ml. Isopropanol (150 ml.) was then added, followed by petrol (60-80) until the mixture was just opaque. The mixture was then allowed to cool to room temperature. The solid which formed was separated by filtration, evaporated with toluene (2×400 ml.) and then washed with ether (300 ml.) to give sodium 2-(2-fluoro-4-bromobenzyl)-1,2-dihydro-1-oxophthalazin-4-ylacetate, 6.5 g., m.p. 244°–247° C.

EXAMPLE 59 (all parts are by weight)

A mixture of 2-(2-fluoro-4-bromobenzyl)-1,2-dihydro-1-oxophthalazin-4-ylacetic acid (50 parts), lactose (27 parts) and maize starch (20 parts) was stirred thoroughly, and a paste formed from maize starch (2 parts) and water (40 parts) was added and thoroughly mixed in. The resultant mass was passed through a 16 mesh screen, then dried at 60° C. and passed through a 20 mesh screen. Magnesium stearate (1 part) was added to the granules obtained, and the whole compressed by conventional means into tablets, containing 10, 20, 50 and 100 mg. of active ingredient and suitable for oral administration for therapeutic purposes.

Using a similar procedure, but replacing the active ingredient by any other compound of the invention or a salt thereof, for example as described in any one of the aforegoing Examples, tablets containing 10, 20, 50 and 100 mg. of active ingredient may be obtained.

What is claimed is:

1. A pharmaceutical composition suitable for use in producing an anti-inflammatory effect in a warm-blooded animal which comprises a compound of the formula:

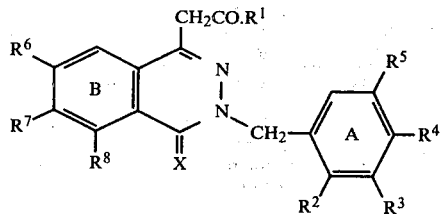

wherein $R^1$ is hydroxy, $R^2$ is fluoro, $R^3$ and $R^5$ are hydrogen and $R^4$ is chloro, bromo or iodo; or $R^2$ and $R^5$ are hydrogen, and $R^3$ and $R^4$ are each independently chloro, bromo or iodo; and in either case $R^6$, $R^7$ and $R^8$ are hydrogen and X is oxygen; or a pharmaceutically acceptable base-addition salt thereof; together with a pharmaceutically acceptable diluent or carrier.

2. The pharmaceutical composition of claim 1 wherein the compound of formula I is selected from the group consisting of 2-(2-fluoro-4-bromobenzyl)-1,2-dihydro-1-oxophthalazin-4-ylacetic acid, 2-(3-chloro-4-bromobenzyl)-1,2-dihydro-1-oxophthalazin-4-ylacetic acid, and the pharmaceutically acceptable base-addition salts thereof.

3. The pharmaceutical composition of claim 1 which is in a form suitable for oral administration, said form being one of a tablet, capsule, suspension or solution.

4. A method for the production of an anti-inflammatory effect in a warm-blooded animal requiring such treatment which comprises administering to said animal a therapeutically effective amount of a compound of formula I, or a pharmaceutically acceptable base-addition salt thereof, as defined in claim 1.

5. The method of claim 4 wherein said compound is selected from the group consisting of 2-(2-fluoro-4-bromobenzyl)-1,2-dihydro-1-oxophthalazin-4-ylacetic acid, 2-(3-chloro-4-bromobenzyl)-1,2-dihydro-1-oxophthalazine-4-ylacetic acid, and the pharmaceutically acceptable base-addition salts thereof.

* * * * *